(12) United States Patent
Tatsumi et al.

(10) Patent No.: US 7,526,947 B2
(45) Date of Patent: May 5, 2009

(54) AUTOMATIC SAMPLE INTRODUCTION APPARATUS

(75) Inventors: Nobuyuki Tatsumi, Kyoto (JP); Morimasa Hayashi, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 422 days.

(21) Appl. No.: 11/360,956

(22) Filed: Feb. 23, 2006

(65) Prior Publication Data

US 2006/0196282 A1 Sep. 7, 2006

(30) Foreign Application Priority Data

Mar. 2, 2005 (JP) ............................. 2005-058124

(51) Int. Cl.
*G01N 30/20* (2006.01)
*G01N 30/24* (2006.01)

(52) U.S. Cl. .................. 73/61.55; 73/61.56; 73/864.84; 422/70

(58) Field of Classification Search ..... 73/61.55–61.56, 73/23.41–23.42, 863.71–863.73, 864.83–864.85, 73/864.87; 422/70
See application file for complete search history.

(56) References Cited

U.S. PATENT DOCUMENTS

| | | | | |
|---|---|---|---|---|
| 3,800,602 | A * | 4/1974 | Jones | 73/23.42 |
| 4,577,492 | A * | 3/1986 | Holba et al. | 73/61.56 X |
| 5,449,902 | A * | 9/1995 | Onishi et al. | 250/288 |
| 5,462,660 | A * | 10/1995 | Singleton et al. | 422/70 X |
| 5,567,307 | A * | 10/1996 | Karmarkar | 210/198.2 |
| 6,296,771 | B1 * | 10/2001 | Miroslav | 506/7 |
| 7,219,566 | B1 * | 5/2007 | Maeda | 73/864 |
| 2002/0132351 | A1 * | 9/2002 | Szecsody | 436/25 |
| 2002/0146349 | A1 * | 10/2002 | Gygi et al. | 422/70 |
| 2002/0190001 | A1 * | 12/2002 | Petro | 210/656 |
| 2006/0045810 | A1 * | 3/2006 | Choikhet et al. | 422/100 |
| 2006/0186028 | A1 * | 8/2006 | Hughes | 422/70 X |

(Continued)

FOREIGN PATENT DOCUMENTS

EP 892267 A1 * 1/1999

(Continued)

OTHER PUBLICATIONS

JPO English abstract of JP 2002-98678 A, Ishii et al., Apr. 2002 □□□□Derwent English abstract of JP 2002-98678 A, Ishii et al., Apr. 2002.*

(Continued)

*Primary Examiner*—Thomas P Noland
(74) *Attorney, Agent, or Firm*—Rankin, Hill & Clark LLP

(57) ABSTRACT

A function of automatically performing a pretreatment process on a sample is provided in an auto sampler of a total volume injection method that can realize high measurement accuracy even when an amount of the sample is small. A multi-port valve and a multi-position valve are connected to each other, and a plurality of kinds of cleaning solutions and also a mobile phase are connected to the multi-port valve. By providing a certain volume in a tube connected to a measuring pump for suctioning the sample, the pump can suction a sufficient amount of the cleaning solution or a diluent solution at one suction operation. Consequently, an apparatus according to the invention can deal with the pretreatment such as cleaning and dilution, without repeating the same suction/discharge operations.

6 Claims, 3 Drawing Sheets

U.S. PATENT DOCUMENTS

2006/0219638 A1* 10/2006 Watanabe et al. ...... 73/61.56 X

FOREIGN PATENT DOCUMENTS

| EP | 1536228 A1 | * | 6/2005 |
|---|---|---|---|
| JP | 6-148157 | | 5/1994 |
| JP | 07318545 A | * | 12/1995 |
| JP | 2001242181 A | * | 9/2001 |
| JP | 2002-98678 | | 4/2002 |
| JP | 2002267643 A | * | 9/2002 |
| JP | 2004-53445 | | 2/2004 |
| WO | WO 2005011832 A2 | * | 2/2005 |

OTHER PUBLICATIONS

JPO English abstract of JP 2004-53445 A, Tatsumi, Feb. 2004☐☐☐☐Derwent English Abstract of JP 2004-53445 A, Tatsumi, Feb. 2004.*

Derwent English Abstract and clipped image of Research Document RD 355080 A, Nov. 1993, "Improved gas chromatograph has ten-port valve to eliminate build-up of valve leakage in the lines", Derwent-ACC-No. 1993-411630.*

"HPLC//LCtalk No. 46, Injection methods of Autosampler (Comparison between Total Volume Injection Method and Partial Injection Method)", http://www.an.shimadzu.co.jp/support/lib/ictalk/46/46tec.htm Jan. 2006, 3 pages, in Japanese.

* cited by examiner

AUTOMATIC SAMPLE INTRODUCTION APPARATUS

This application claims foreign priority based on Japanese Patent application No. 2005-058124, filed Mar. 2, 2005, the contents of which is incorporated herein by reference in its entirety.

BACKGROUND OF THE INVENTION

1. Field of the Invention

The present invention relates to a sample introduction apparatus for introducing a sample into an analyzer such as a liquid chromatograph, and more particularly, to a sample introduction apparatus suitable for analysis with pretreatment.

2. Description of the Related Art

Mainly, there are two injection methods in an automatic sample introduction apparatus (also referred to as an autosampler or an autoinjector) for liquid chromatograph. One is a "total volume injection method," in which a total volume of a sample measured and taken from a sample bottle (vial) is injected, and the other is a "partial injection method," in which a part of the sample measured and taken from the sample bottle is filled in a sample loop and then injected (for example, refer to "HPLC//LCtalkNo.46, Injection methods of Autosampler (Comparison between Total Volume Injection Method and Partial Injection Method)," Shimadzu Corporation, online, http://www.an.shimadzu.co.jp/support/lib/lctalk/46/46tec.htm, searched on Feb. 21, 2005).

The sample introduction apparatus in the "total volume injection method" uses a sample loop for sample measurement, the sample loop having a needle for sample introduction which is provided at a tip portion thereof, and inserts the needle into the sample bottle. Then, the apparatus sample introduction apparatus suctions the sample into the sample loop by using a syringe, and measures the sample. Subsequently, the apparatus connects the needle to a sample introduction port of the liquid chromatograph, and changes a flow path to feed a mobile phase from the needle to a column through the sample loop. Thus, the apparatus performs sample introduction (for example, refer to JP-A-6-148157).

Since an accuracy of injection amount at the time of the sample injection is high, and there is no loss of the sample due to the total volume injection of the measured sample, the sample introduction apparatus for introducing the sample, such as the liquid chromatograph, often employs the "total volume injection method."

According to a purpose of analysis or a sample to be analyzed, pretreatment is performed on the sample. This pretreatment is such as concentration control of the sample, addition of an internal standard substance, or formation of a derivative, for example. Such a pretreatment of the sample is performed before the sample bottle is set in the sample introduction apparatus. For example, in an analysis using the liquid chromatograph, there is case where the sample is preliminarily derivatized to a predetermined substance so as to facilitate the detection of the sample. In this case, a prepared sample obtained by mixing the sample and a derivatization reagent to thereby cause a reaction therebetween is introduced into a high-performance liquid chromatograph through the sample introduction apparatus.

In the total volume injection method, cleaning fluid fills inside of the sample loop when inside of the needle is cleaned with the cleaning fluid. Thus, a part of the cleaning fluid may be injected into a flow path of the mobile phase. In a case where the cleaning fluid differs in composition from the mobile phase, it is difficult to clean the inside of the needle sufficiently. Therefore, when the pretreatment is performed on the sample, a sample introduction apparatus in an injection method in which the needle is placed outside the flow path of the mobile phase, that is, the "partial injection method," is often used. Consequently, in the analysis with the pretreatment of the sample, measurement accuracy deteriorates.

In order to employ the "total volume injection method" in the analysis which requires the pretreatment, an operation can be considered in which the sample, on which the pretreatment is performed, is fed into the sample bottle and then the sample bottle is installed in the sample introduction apparatus. However, this operation is not efficient, since the number of samples is large, the effect of performing the pretreatment varies with time (for example, deterioration of the sample and the mobile phase), and there are losses of the sample and the mobile phase.

SUMMARY OF THE INVENTION

In some implementations, an automatic sample introduction apparatus of the invention comprises: a sample loop for measuring a sample; a needle for injecting the sample, said needle being provided at a tip portion of the sample loop; a measuring pump; a multi-position valve; and a first multi-port valve, wherein the multi-position valve includes: a first port connected to the first multi-port valve; a second port connected to a solution of a mobile phase; a third port connected to a cleaning solution; and a common port connected to the measuring pump, the multi-position valve has a state in which the common port is communicated with anyone of the ports by switching, and a state in which any two of the ports are communicated with each other, the first multi-port valve includes: a fourth port connected to the sample loop; a fifth port connected to a flow path on an upstream side that supplies the mobile phase; a sixth port connected to a flow path on a downstream side including a column; a seventh port connected to a sample introduction port; and an eighth port connected to the multi-position valve to which the measuring pump is connected, and the first multi-port valve has an injection state in which a flow path is formed in which the mobile phase flows to the column through the sample loop, the needle and the sample introduction port, and a load state in which a flow path is formed in which the mobile phase flows to the column without flowing through the sample loop, the needle, and the sample introduction port.

The automatic sample introduction apparatus of the invention further comprises: a retention mechanism for retaining the sample introduced into the sixth port of the first multi-port valve.

In the automatic sample introduction apparatus of the invention, the retention mechanism includes a second multi-port valve and a retention tube, the second multi-port valve includes: a ninth port connected to the first multi-port valve; a tenth port connected to the flow path on the downstream side including the column; an eleventh port connected to one end of the retention tube; and a twelfth port connected to other end of the retention tube, and the second multi-port valve has a state in which only the ninth port and the tenth port are communicated with each other, and a state in which the ninth port, the tenth port, the eleventh port and the twelfth port are communicated with one another.

Furthermore, the automatic sample introduction apparatus of the invention further comprises: a temperature adjusting mechanism (especially heating) for the second multi-port valve and the retention tube.

According to the automatic sample introduction apparatus of the invention, the total volume injection method in which the measurement accuracy is high is employed so as to ensure the injection accuracy, while the pretreatment such as dilution of the sample, addition of a reagent, and reaction between an additive and the sample can be performed. Thus, the loss of the sample due to the pretreatment can be prevented. Furthermore, the apparatus according to the invention can deal with various kinds of cleaning.

DESCRIPTION OF THE PRFERRED EMBODIMENTS

Figure 1:
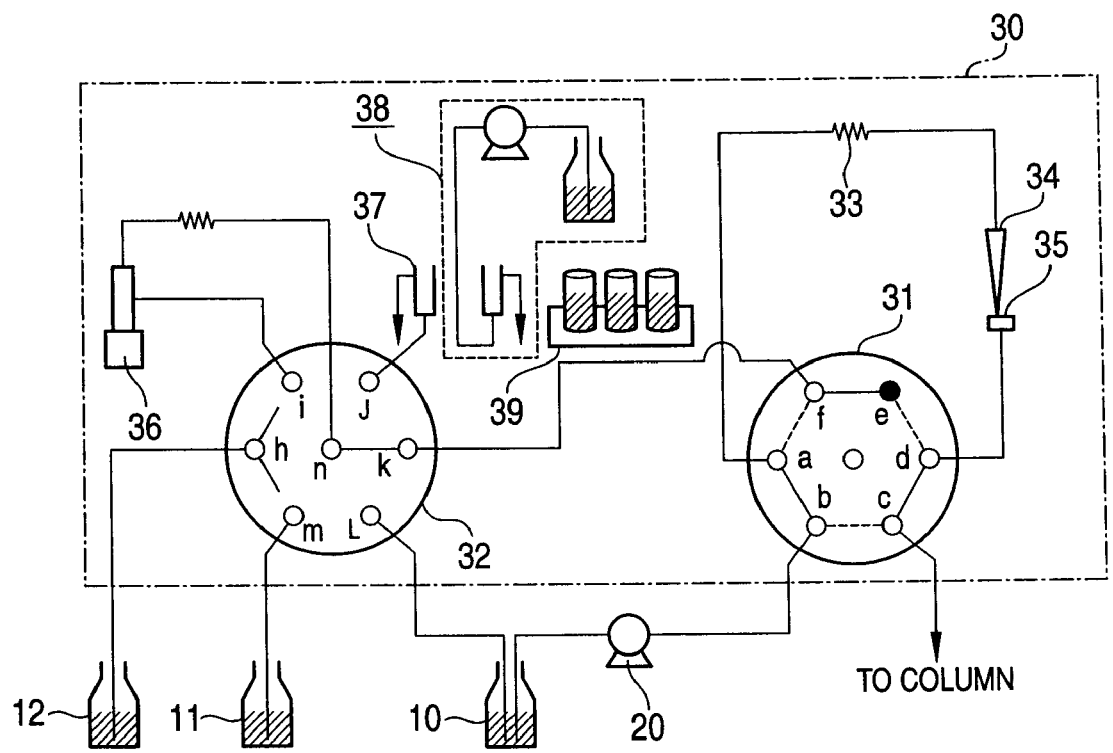
FIG. 1 is a diagram illustrating an embodiment of the invention.

FIG. 1 shows an embodiment of an automatic sample introduction apparatus according to the invention, in a case where the automatic sample introduction apparatus is used for a liquid chromatograph.

A mobile phase solution is delivered from a reservoir 10 by a liquid transfer device 20, and flows into a multi-port valve 31 of an automatic sample introduction apparatus 30. In the multi-port valve 31, a port a is connected to a sample loop 33 having a needle 34 at a tip portion thereof, a port b is connected to the liquid transfer device 20 such as a pump, a port c is connected to a flowpath on a downstream side including a column (not shown), a port d is connected to a sample introduction port 35, and a port f is connected to a multi-position valve 32. A port e of the multi-port valve 31 is used in a case where a function of a reaction caused by heating is provided as a pretreatment which will be described later. Incidentally, the port e is connected to a stop joint, a check valve, etc. so as to block the port when not used. A state of the multi-port valve 31 is appropriately changed between a load state (indicated by dashed lines in FIG. 1) in which the ports of each of the pairs a-f, e-d, and b-c are communicated with each other, and an injection state (indicated by solid lines in FIG. 1) in which the ports of each of the pairs a-b, c-d, and e-f are communicated with each other.

When the multi-port valve 31 is in the load state, a port k and a common port n of the multi-position valve 32 are communicated with each other. Also, the sample loop 33 and the needle 34, which are connected to the port a of the multi-port valve 31, are moved with respect to a sample placed on a sample tray 39 by a needle moving section (not shown). The sample is suctioned through the needle 34 into the sample loop 33. Subsequently, the needle 34 is moved so as to be inserted in the sample injection port 35. Then, the state of the multi-port valve 31 is changed to the injection state. Consequently, a flow path is formed in which the mobile phase solution flows from the reservoir 10 to the column through the sample loop 33, the needle 34, and the sample introduction port 35. Thus, the total volume of the measured sample is introduced.

In the multi-position valve 32, a port L is connected to a flow path including the reservoir 10, ports m and h are respectively connected to different cleaning solution storage containers 11 and 12, a port J is connected to a cleaning pot 37, and a port i is connected to a measuring pump 36. The measuring pump 36 is connected to the common port n so that the measuring pump 36 can suction a plurality of kinds of cleaning solutions and the mobile phase solution. Incidentally, the measuring pump 36 is, for example, a plunger pump. Consequently, the solution left in the flow path when the cleaning with the plurality of kinds of cleaning solutions is performed can be replaced with a solution whose composition is the same as that of the mobile phase. In FIG. 1, a tube connected to the measuring pump 36 has a certain volume so as to enhance cleaning effect. Also, a cleaning unit 38 including a cleaning solution, a liquid transfer device, a cleaning pot, and a drain is provided in the automatic sample introduction apparatus 30 so as to perform the cleaning of the exterior of the needle.

Figure 4:
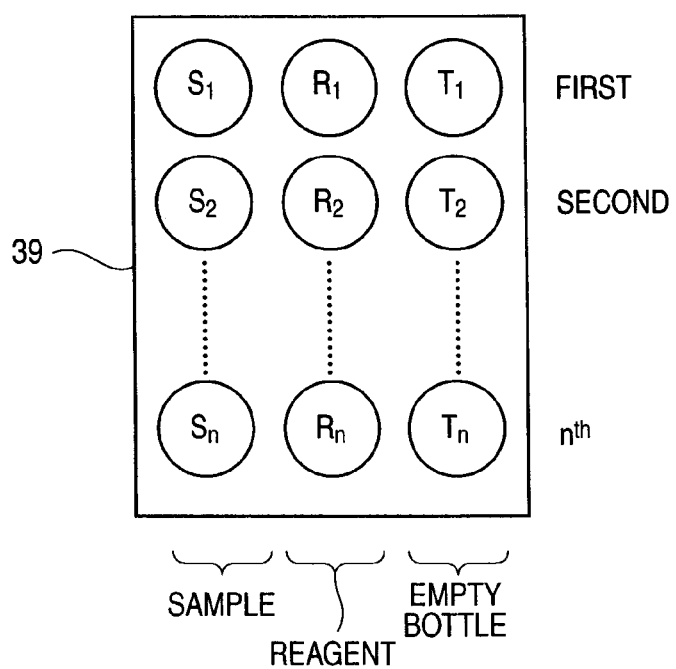
FIG. 4 is a diagram illustrating a state in which bottles of a sample, etc. are arranged on a sample tray.

FIG. 4 is a schematic diagram illustrating an arrangement of sample bottles on the sample tray 39. On the sample tray 39, there are bottles each of which contains a sample $S_1$ to $S_n$ to be analyzed, respectively, bottles each of which contains a reagent $R_1$ to $R_n$, respectively, to be mixed with the sample S to facilitate the separation and the detection of the sample S, and bottles $T_1$ to $T_n$ that are initially empty. The reagent R is used so that the sample S reacts with the reagent R in a pretreatment process and the analysis of the sample S is facilitated. Thus, the same reagent R may be contained in the bottles $R_1$ to $R_n$.

Hereinafter, an operation of each part of the automatic sample introduction apparatus according to the invention in a case of performing the pretreatment is described.

The needle 34 performs an operation for suctioning the sample $S_1$. The multi-port valve 31 is brought into the load state, and the common port n and the port k of the multi-position valve 32 are communicated with each other. The needle 34 is inserted into the bottle containing the sample $S_1$ on the sample tray 39, and suctions the sample $S_1$ by a suction operation of the measuring pump 36. Subsequently, the needle 34 is moved to above the bottle $T_1$ on the sample tray 39, and the sample $S_1$ is discharged by a discharge operation of the measuring pump 36. The mobile phase that contacts with the sample in the flow path is also discharged so that the suctioned sample is totally discharged, that is, so as to enhance the measurement accuracy.

Subsequently, the needle 34 is moved to the cleaning pot 37. The common port n and the port m of the multi-position valve 32 are communicated with each other, and the measuring pump 36 suctions a cleaning solution 11a in the cleaning solution storage container 11. Then, the multi-position valve 32 is switched so that the common port n and the port k are communicated with each other, and the suctioned cleaning solution 11a is discharged from the needle 34 to the cleaning pot 37. Consequently, the sample component left in the inside of the needle 34 and the sample loop 33 is discharged, and the inside of the needle 34 and the sample loop 33 can be cleaned.

Similarly, when the measuring pump 36 suctions the mobile phase solution in the reservoir 10 and the needle 34 discharges the suctioned mobile phase solution, the cleaning solution left in the inside of the needle 34 and the sample loop 33 can be replaced with the mobile phase solution. Then, the needle 34 is moved to the cleaning pot of the cleaning unit 38, and the exterior of the needle is cleaned.

A similar operation is performed on the reagent $R_1$, so that the sample $S_1$ and the reagent $R_1$ is mixed in the bottle $T_1$. In order to prevent occurrence of unevenness of concentration in the mixed liquid, positive mixing of the sample $S_1$ and the reagent $R_1$ is necessary. After the solution of the reagent $R_1$ is discharged into the bottle $T_1$, air is suctioned through the needle 34 to the extent that the mixed liquid and the mobile phase do not contact with each other. Thereafter, the suction and the discharge of the mixed liquid are appropriately repeated. Then, after the process of cleaning the needle 34 and the sample loop 33, the mixed liquid is suctioned through the needle 34. Subsequently, the needle 34 is moved so as to be inserted into the sample injection port 35. Then, the state of the multi-port valve 31 is changed to the injection state.

Figure 2A:
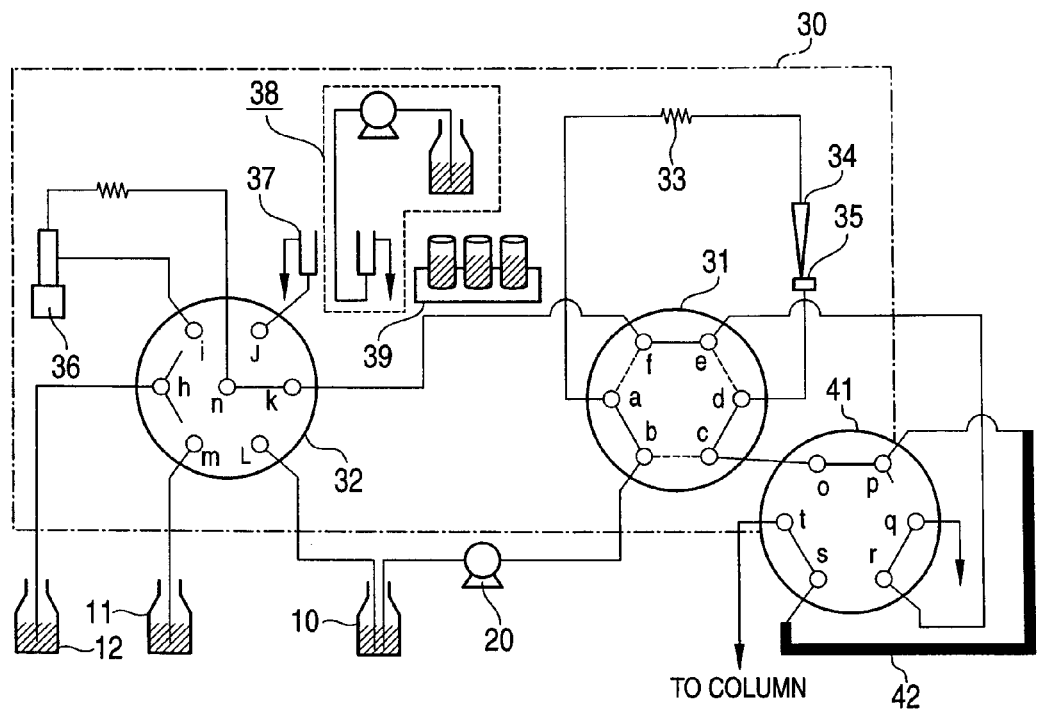
FIGS. 2A and 2B are diagrams each illustrating a flow path having a reaction tube further provided in a pretreatment part of an embodiment of the invention.

In a case where only dilution is performed as the pretreatment, it is sufficient to configure the automatic sample injection apparatus as described above. However, in a case where the pretreatment involves a reaction, it may be necessary to delay a time that the mixed liquid actually arrives at the column. In FIG. 2A, the mixed liquid introduced through the needle 34 is retained in a retention tube 42 (a reaction tube in which the reaction is performed) connected to a second multi-port valve 41.

Figure 2B:
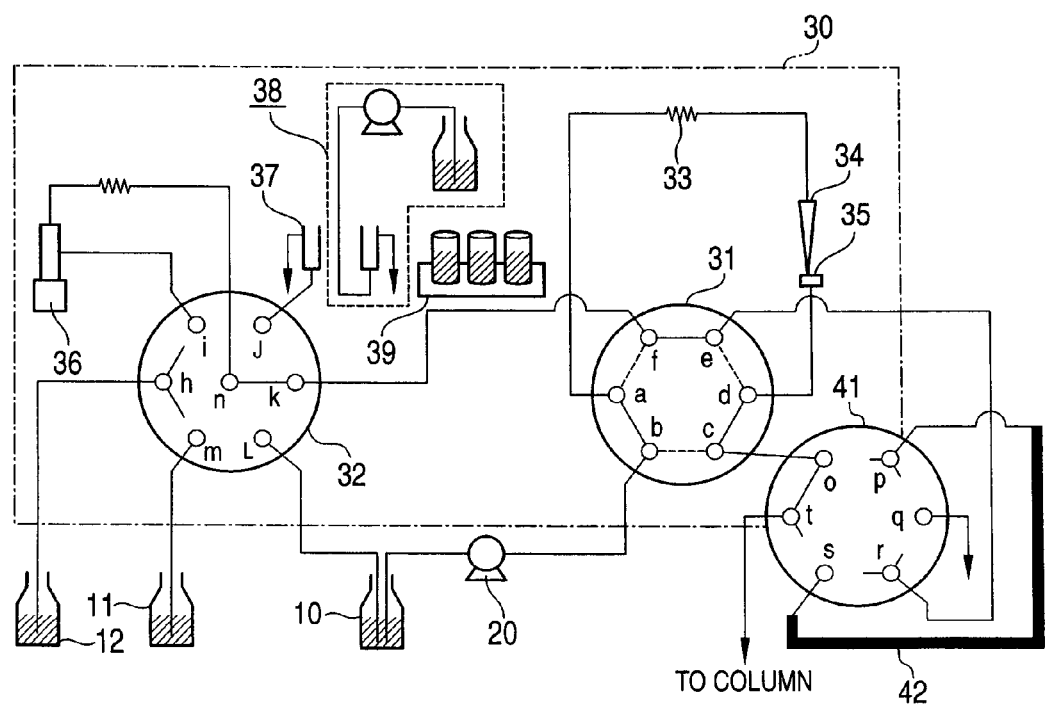

The second multi-port valve 41 has a state (FIG. 2A), in which a port o connected to the port c of the multi-port valve 31 is communicated with ports p, s, and t connected to the reaction tube 42 and the flow path on the downstream side including the column, and the port e of the multi-port valve 31 is communicated with the multi-port valve 41. The second multi-port valve 41 also has a state (FIG. 2B), in which the port o connecting to the port c of the multi-port valve 31 is communicated with only the port t connected to the flow path on the downstream side including the column. In the second multi-port valve 41, a flow path communicating the port o which is connected to the port c of the multi-port valve 31 with the ports p and s, which are connected to one end of the reaction tube 42 respectively, or a flow path communicating the port o with the ports s and t, which are connected to the flow path on the downstream side including the column, is set to be longer than a flow path communicating other ports with each other. Consequently, a state is available in which both ends of the reaction tube 42 for performing the reaction on the mixed liquid can be blocked, without interrupting the transfer of the liquid from the liquid transfer device 20. Thus, the reaction on the mixed solution can be performed online as the pretreatment, without causing the sample to flow out to the downstream side.

Figure 3:
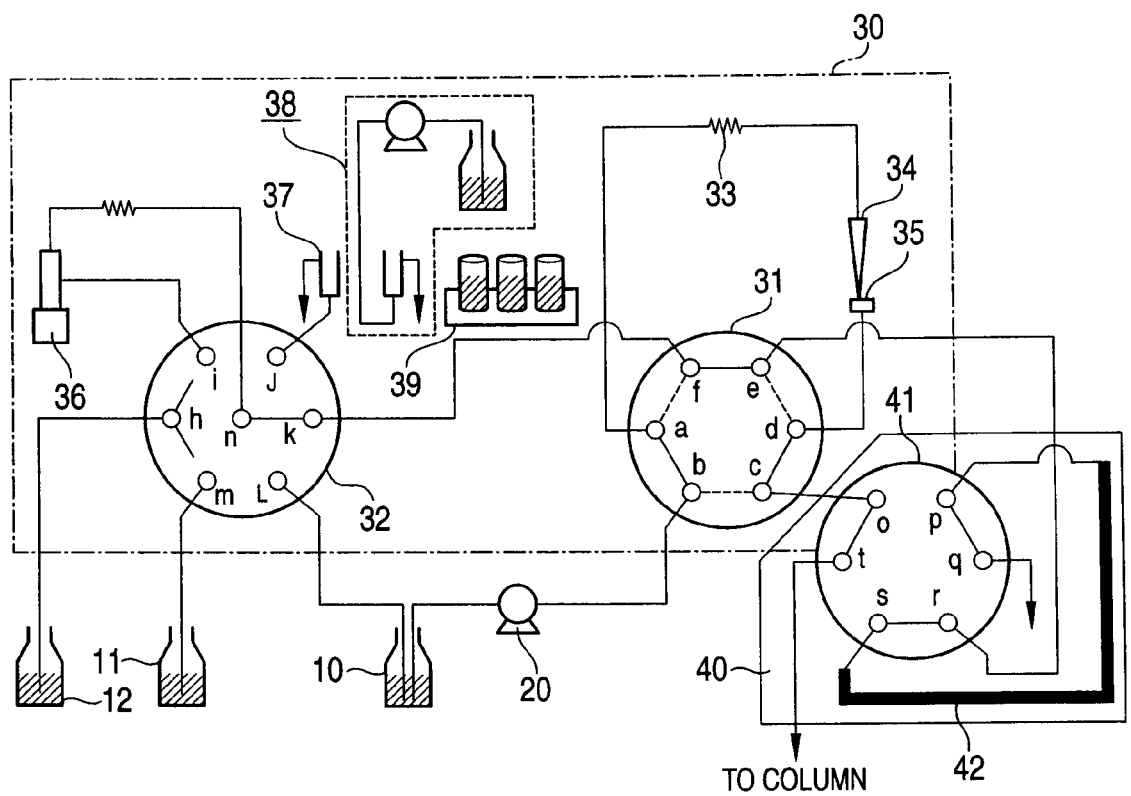
FIG. 3 is a diagram illustrating a flowpath further having a mechanism for heating the reaction tube further provided in an embodiment of the invention.

As shown in FIG. 3, by providing a heater 40 (for example, a block heater) for heating the reaction tube 42, the pretreatment can be performed under heating condition. Also, since both ends of the reaction tube are blocked as described above, internal pressure of the retention tube rises and boiling point rises when the heat is applied. Thus, the treatment can be performed at a higher temperature. In the case of providing the heater, enhancement of the cleaning effect can be expected by providing the solution and the flow path of the cleaning unit 38 in the heater.

Incidentally, each of the embodiments is an example of the apparatus according to the invention. It is apparent that various appropriate modifications and alterations may be made without departing from the spirit and scope of the invention. Although the embodiments of the invention are described as the apparatus performing the pretreatment, a function of a related automatic sample introduction apparatus may appropriately be provided. For example, there is a related automatic sample introduction apparatus in which the function of a fraction collector is provided. The function of the fraction collector can be provided in the apparatus according to the invention.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. An automatic sample introduction apparatus comprising:
    a sample loop for measuring a sample;
    a needle provided at a tip portion of the sample loop;
    a measuring pump;
    a multi-position valve;
    a first multi-port valve; and
    a tray, for loading thereon a first bottle for containing the sample, a second bottle for containing a solution to be mixed to the sample, and a third bottle for containing a mixed solution which is obtained by mixing the sample and the solution,
    wherein the multi-position valve includes:
    a first port connected to the first multi-port valve;
    a second port connected to a mobile phase;
    a third port connected to a cleaning solution; and
    a common port connected to the measuring pump,
    the multi-position valve has a state in which the common port is communicated with any one of the ports by switching, and a state in which any two of the ports are communicated with each other,
    the first multi-port valve includes:
    a fourth port connected to the sample loop;
    a fifth port connected to a flow path on an upstream side that supplies the mobile phase;
    a sixth port connected to a flow path on a downstream side including a column;
    a seventh port connected to a sample introduction port; and
    an eighth port connected to the multi-position valve to which the measuring pump is connected,
    the first multi-port valve is configured to be selectively placed in one of an injection state in which a flow path is formed in which the mobile phase flows to the column through the sample loop, the needle and the sample introduction port, and a load state in which a flow path is formed in which the mobile phase flows to the column without flowing through the sample loop, the needle, and the sample introduction port, and
    the automatic sample introducing apparatus is configured to move the needle to the tray to mix the sample and the solution by performing the switching operation of the multi-position valve while placing the first multi-port valve in the load state, and then to place the first multi-port valve in the injection state after moving the needle, into which the mixed solution has been sucked, to the sample introduction port.

2. The automatic sample introduction apparatus according to claim 1, further comprising:
    a retention mechanism for retaining the sample introduced into the sixth port of the first multi-port valve.

3. The automatic sample introduction apparatus according to claim 2,
    wherein the retention mechanism includes a second multi-port valve and a retention tube,
    the second multi-port valve includes:
    a ninth port connected to the first multi-port valve;
    a tenth port connected to the flow path on the downstream side including the column;
    an eleventh port connected to one end of the retention tube; and
    a twelfth port connected to other end of the retention tube, and the second multi-port valve has a state in which only the ninth port and the tenth port are communicated with each other, and a state in which the ninth port, the tenth port, the eleventh port and the twelfth port are communicated with one another.

4. The automatic sample introduction apparatus according to claim 2, further comprising;

a heater for heating the retention mechanism.

5. An automatic sample introduction apparatus comprising:

a sample loop for measuring a sample; a needle for injecting the sample, said needle being provided at a tip portion of the sample loop;

a measuring pump;

a multi-position valve;

a first multi-port valve; and a retention mechanism, wherein the multi-position valve includes:

a first port connected to the first multi-port valve;

a second port connected to a solution of a mobile phase;

a third port connected to a cleaning solution; and a common port connected to the measuring pump, the multi-position valve has a state in which the common port is communicated with any one of the ports by switching, and a state in which any two of the ports are communicated with each other, the first multi-port valve includes:

a fourth port connected to the sample loop;

a fifth port connected to a flow path on an upstream side that supplies the mobile phase;

a sixth port connected to a flow path on a downstream side including a column;

a seventh port connected to a sample introduction port; and an eighth port connected to the multi-position valve to which the measuring pump is connected, and the first multi-port valve has an injection state in which a flow path is formed in which the mobile phase flows to the column through the sample loop, the needle and the sample introduction port, and a load state in which a flow path is formed in which the mobile phase flows to the column without flowing through the sample loop, the needle, and the sample introduction port, and the retention mechanism is configured to retain the sample introduced into the sixth port of the first multi-port valve.

6. The automatic sample introduction apparatus according to claim 5, wherein the retention mechanism includes a second multi-port valve and a retention tube, the second multi-port valve includes:

a ninth port connected to the first multi-port valve;

a tenth port connected to the flow path on the downstream side including the column;

an eleventh port connected to one end of the retention tube; and a twelfth port connected to other end of the retention tube, and the second multi-port valve has a state in which only the ninth port and the tenth port are communicated with each other, and a state in which the ninth port, the tenth port, the eleventh port and the twelfth port are communicated with one another.

\* \* \* \* \*